United States Patent [19]

Denney

[11] 4,105,408

[45] Aug. 8, 1978

[54] UREA ASSAY

[75] Inventor: Jerry W. Denney, Carmel, Ind.

[73] Assignee: American Motor Corporation, Indianapolis, Ind.

[21] Appl. No.: 841,655

[22] Filed: Oct. 13, 1977

Related U.S. Application Data

[62] Division of Ser. No. 740,612, Nov. 10, 1976.

[51] Int. Cl.$^2$ ............................................. G01N 33/16
[52] U.S. Cl. ............................. 23/230 B; 260/239 BD
[58] Field of Search ................. 23/230 B; 260/239 BD

[56] References Cited

U.S. PATENT DOCUMENTS 3,890,099  6/1975  Jung ................................... 23/230 B

*Primary Examiner*—Morris O. Wolk
*Assistant Examiner*—Arnold Turk
*Attorney, Agent, or Firm*—Robert A. Spray

[57] ABSTRACT

A urea assay or analysis process and reagents therefor, in which the assay involves a reaction between a sample of biological fluid and an acidic reagent solution of o-phthaldehyde and a chromogenic compound; the chromogenic compounds include certain substituted benzene compounds, certain substituted naphthalene compounds, certain aminopyrimidines, certain substituted quinolines, certain morpholino substituted quinolines and certain morpholino substituted naphthalenes.

3 Claims, No Drawings

UREA ASSAY

This is a division of U.S. Patent application, Ser. No. 740,612, filed Nov. 10, 1976.

INTRODUCTION

The present invention relates to the quantitative analysis of urea in body fluids, such as blood plasma, serum, urine and cerebrospinal fluids.

VITAL SIGNIFICANCE OF ACCURATE AND RELIABLE UREA MEASUREMENTS

Urea is the major end product of protein catabolism in man, being the primary vehicle for the removal of toxic quantities of ammonia from the system. Urea is a product which is principally formed in the liver and excreted by the kidneys.

Thus measurements of urea in various body fluids provide the medical clinician with a very valuable diagnostic indicator, e.g., as an important measurement to assess kidney function or dysfunction and associated disease states. Its measurement in serum is also used to provide an accurate indication of proper levels of protein intake and concommitant catabolism.

Generally, increased levels of urea are diagnostically significant. E.g., they are associated with nephritis, renal ischemia, urinary tract obstructions, and certain extrarenal disorders such as congestive heart failure, certain liver diseases, and diabetes.

Decreased levels of urea likewise are diagnostically significant. That is, they may indicate acute hepatic insufficiency or may result from overvigorous parenteral fluid therapy.

Changes, whether up or down, and even of a relatively small amount, are important. E.g., when following the progress of a particular disease state, it is imperative that accurate assays for urea be provided to the medical clinician so that early trends may be detected and treated, before worse and even potentially life-threatening conditions are allowed to occur. Thus accuracy should be sufficient that detection is made of small percentage changes. Therapeutic measures can be closer controlled by accurate determination of changes, even changes of a small percentage increment.

Although the great importance of accurate and reliable urea assays has been known for many years, the potential and future importance of accurate assessments of urea concentrations will likely continue to rise as newer drugs to combat a variety of human diseases are introduced to medical practice; for experience has shown that many new drugs produce toxic side effects, and if such drugs are given in excess, they may lead to serious consequences to the patients' welfare as well as increased hospitalization; thus excess dosage or the hypersensitivity of a patient to a particular drug may be established by accurate measurements of urea, thereby preventing or minimizing adverse therapeutic reactions.

DISADVANTAGES OF PRIOR ART

An early urea measurement was that of Marshall.[1] As early as 1913, Marshall used the enzyme urease as a tool for the determination of urea in blood. The method consisted of incubation of the blood with urease, an enzyme which breaks down urea into one molecule of carbon dioxide and two molecules of ammonia, isolation of the ammonia thus liberated by aeration, and quantitation of the ammonia by titration as an indication of the quantity of urea.

Nessler's reagent[2] was probably the most common reagent of those which were used as an indication of ammonium ions ($NH_4^+$) present, but Nessler's method presented the burdensome restriction of photometrically reading the color developed within a 1 minute time frame due to the formation of color by constituents other than $NH_4^+$ ions reacting with the reagent, leading to possible inaccuracy due to overestimation of the amount of urea.

Subsequent to the method of Marshall, a plethora of new methods have been suggested and attempted, due to the increasing awareness of the vital significance of accurate, reliable, and reproducible urea measurements, and due to the fact that none overcame all disadvantages without introducing new ones.

These methods possessed the commonality of the enzyme urease, and differed only in the means of detection of the ammonia formed.

Perhaps the most widely used of the enzymatic methods was that which employed the Berthelot reaction[3] in which serum is treated with urease for about 15 minutes, and then two additional reagents are added to the mixture at an elevated temperature to produce the desired indicator reaction.

However, there continued to be disadvantages and difficulties with the entire class of methods which utilize an enzymatic breakdown of urea. Main disadvantages were the extended incubation times necessary to fully react the urea in the sample, and the stability difficulties of the reagent system; and perhaps the most serious disadvantage was the fact that these methods were not very well suited to the measurements of urinary urea, for large amounts of free ammonia may be present in these samples and would be mistakenly measured as urea, which would lead to overestimation and consequent erroneous diagnosis and treatment.

Even though the enzymatic methods were disadvantageous, the prior art methods for many years continued to have that basic nature, even with those disadvantages inherent in those methods; for the prior art has long realized the benefits of urea assays, and even disadvantageous ones were believed better than none at all, as the prior art continued to try to achieve an advantageous urea assay.

In 1939, Fearon[4] departed from the urease enzyme methodologies, and showed that urea reacts with diacetyl monoxime at elevated temperatures in the presence of a strong acid and an oxidizing agent to produce a chromogen. Ormsby[5] in 1942 applied to Fearon reaction to measure blood and urine urea in a protein-free solution. Although these methodologies which employ the use of the Fearon reaction have gained rather wide acceptance today, especially in connection with the use of automated chemical analyzers, they suffer one or more of the disadvantages and drawbacks of: 1, the color developed is photosensitive, thus requiring that the test be performed under controlled and minimal lighting conditions; 2, the lack of conformity to Beer's law, thus requiring the use of multiple standards; 3, the unpleasant nature of the reagents; 4, the fact that the reaction is not completely specific for urea, leading to inaccurate assays when interfering substances are present; and in many and perhaps even the majority of cases, the technician would not be aware of the presence of these substances, and thus would not suspect any cause for inaccuracy of the measurement; and, 5, requirements of rigid temperature control and the use of very elevated reaction temperatures.

Although the Fearon method is perhaps the most widely used method today, the use of elevated reaction temperatures and the acidic nature of the reagents represents particular hazards when used in continuous flow analysis equipment due to the buildup of pressure and the concommitant possibility of disruption of plumbing, causing hot acid to be propelled into the air and with serious consequences to the eyesight of laboratory personnel.

Subsequent to 1942, various investigators of the prior art have proposed still other departures or approaches for the measurment of urea, including the manometric techniques (measurement of the pressure of gases released in the reaction sequence). However, none have gained widespread acceptance, probably due to such disadvantages as the complexity of the method or the requirement of expensive and troublesome equipment.

Thus, for many years, the prior art has struggled in various manners, and with differing approaches, in its attempts to discover a desirable urea measurement assay.

Other attempts by the prior art, in this long struggle for a satisfactory and successful urea determination, have long included an attempt to utilize the reaction between urea and an aldehyde to achieve a colored reaction product or a reaction product which becomes colored when reacted with a chromogen.

One of the earliest of these methods, attempting the use of an aldehyde, apparently was that of Brown, who attempted a urea determination by the use of its reaction with p-dimethylaminobenzaldehyde (DMAB).[6]

However, despite the investigations of many others of the prior art[7], problems which were persistent with this approach of Brown were the potential interferences with these methods by commonly used drugs (with the attendant possibility of misdiagnosis) and the sensitivity of the final color developed to temperature fluctuation (necessitating expensive laboratory equipment to assure color stability during the measurement of absorbance).

In 1973, still attempting a more desirable determination based on an aldehyde reaction, Morin and Prox[8] presented a method based on the reaction between urea and the aldehyde, p-dimethylaminobenzaldehyde (DMAB) in which they attempted to quantitate urea directly (without the need for removal of the protein from the specimen) by measuring the absorbance of the chromophore developed with the aldehyde. While the elimination of the necessity for protein removal was an improvement, the method of Morin and Prox still suffered the problem of interference from commonly used drugs.

In 1975, Jung, et al.[9] and Jung's U.S. Pat. No. 3,890,099 reacted urea with a different aldehyde, namely, o-phthalaldehyde, and then went one step further and coupled the product of this reaction with N-(1-naphthyl)ethylenediamine dihydrochloride. Although Jung's approach has certain advantages over other prior art, in that at least it does not require elevated temperatures for the development of the chromophore, it has drawbacks and disadvantages as now summarized.

First, the Jung method requires N-(1-naphthyl)ethylenediamine dihydrochloride. This is a material which is synthesized from α-naphthylamine, and thus likely may contain at least trace amounts of α-naphthylamine, a compound which is widely known as a potent carcinogen (a cancer-causing agent).[10]

Further, as a possible hazard and disadvantage of the Jung method's requirement of the N-(1-naphthyl)ethylenediamine dihydrochloride, there is the disadvantage and danger of the unknown effect of the storage of that compound in the acid required in the reagent, which may decompose the N-(1-naphthyl) ethylenediamine dihydrochloride, yielding the aforementioned carcinogenic α-naphthylamine.

Thus, there is the possible presence of α-naphthylamine in the laboratory, with its attendant risks to the immediate and long term health of laboratory personnel.

Moreover, the Jung method shows significant interference from a class of drugs, specifically sulfa drugs, which are commonly used to treat the specific disease states to which measurements of urea are used as a crucial diagnostic test; and thus the urea is mistakenly overestimated to a certain extent in the presence of those drugs, leading to unreliability and inaccuracy of the urea measurement.

The present invention is a distinct departure from the several prior art methodologies, and it overcomes many of the disadvantages of prior art methodologies. More specifically, in the assay of the present invention, the reagents are stable, the color reaction obeys Beer's law over a wide range of urea concentrations, does not require the use of elevated reaction temperatures or uncommon laboratory apparatus, shows significant immunity to interferences common to older methodologies, especially to drug-induced interference, and is extremely rapid (requiring less than 5 minutes to complete an analysis).

THE PRESENT INVENTION AND ITS ADVANTAGES SUMMARIZED

This invention relates to a process for the quantitative measurement of urea in aqueous or protein based samples. More particularly, the invention relates to the discovery of major classes of chromogenic compounds which will react with the condensation product of urea and o-phthalaldehyde, achieving more sensitive, specific, and thereby accurate assays for urea, by producing a chromophore having very desirable characteristics for clinical assays for urea.

The present invention overcomes the problems encountered in prior art in that the chromophore is not photosensitive, and provides stable reagents for the assay.

A further inherent advantage of the present invention is that it measures urea and not free ammonium ion, thus making the method adaptable to the measurement of urinary urea without costly and time-consuming pretreatment of the sample.

Further, in the present invention, the reaction obeys Beer's law (i.e. concentration versus absorbance readings are in direct linear proportion) over a wide range of urea concentrations, thus reducing the possibility of error and allowing less occurrences of repeat analyses, thereby providing the clinician with more reliable results with a minimum of costly delay.

A further advantage of the present system over the Jung method is the fact that the present invention shows very little interference from drugs which are commonly used to treat the diseases for which the measurement of urea is used to detect and monitor.

DESCRIPTION OF THE PREFERRED EMBODIMENTS

In a preferred embodiment of the present invention, a sample of a body fluid containing urea is added to a reaction tube; and to it are added an acidic solution of o-phthalaldehyde, and an acidic solution containing one of the general classes of chromogenic compounds listed below and given as examples. Chromophore development begins immediately; and the rate of color development may be hastened, if desired, by incubation of the reaction mixture at 37° C. Within a 3 to 5 minute period, enough color is developed so that photometers commonly found in clinical laboratories may be used to measure the amount of color formed. The amount of urea present in the original sample is calculated by comparing the absorbance of the patient's sample to the absorbance shown by a similarly treated standard solution of urea, the concentration of which is accurately known.

The o-phthalaldehyde reagent is prepared by adding from 200 mg of a o-phthalaldehyde to an aliquot of approximately 3.75 N sulfuric acid. To this mixture is desirably added a quantity of polyoxyethylene lauryl ether (such as BRIJ 35) or alkylaryl polyether (such as TRITON) or other nonionic surface active agents such that the final concentration of the surfactant is approximately 1-3% (w/v). The mixture is then made up to a final volume of one liter.

This description will yield a reagent with a concentration of the major reactive ingredient, o-phthalaldehyde, which will produce accurate and sensitive assays of urea in body fluids.

One may alter the concentration of o-phthalaldehyde within parameters given herein, depending upon the particular application of the reagent system. For instance, it has been found that increasing the concentration of o-phthalaldehyde in this reagent will lead to significant rises in the rate of color development. Thus, for the laboratory analyst who possesses high speed chemmical analyzers, it would be desirable to increase the concentration of the reagent so that the color may be developed and measured rapidly, thereby increasing the productivity or throughput of the analysis. Conversely, if the procedure is to be run manually by a technician, it would be desirable to lower the concentration of this reagent in order to allow sufficient time for the analyst to accomplish the steps necessary to process multiple samples in an orderly fashion.

Thus it may be seen that the final concentration of the reagent employed will vary depending upon the particular application involved, although all concentrations within the parameters given will lead to accurate and precise assays.

It has been found that there are six major classes of compounds which function as chromogenic compounds in this reaction. They are as follows:

(1.) 1,3 or 1,3,5 di- or tri-substituted hydroxy or methoxy benzene compounds, which have the following general structure:

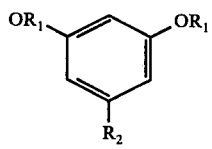

where $R_1$ = —H or —CH$_3$ and
where $R_2$ = —H, or —OH, or —OCH$_3$

Examples of this class are:
  (a) 1,3-dihydroxybenzene
  (b) 1,3,5-trihydroxybenzene
  (c) 1,3-dimethoxybenzene (2.) 1, or 1,3 mono- or di-substituted hydroxy or methoxy naphthalene compounds which have the following general formula:

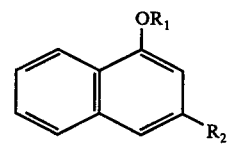

where $R_1$ = —H or —CH$_3$ and
where $R_2$ = —H, or —OCH$_3$, or —OH.

Examples of this class of compounds are:
  (a) (1,3-dihydroxynaphthalene)
  (b) (1-hydroxynaphthalene)

(3.) 4 or 4,6 substituted 2-aminopyrimidines, where the substituting group is an electron withdrawing group possessing the following general structure:

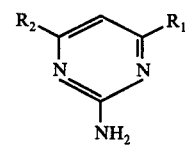

where $R_1$ is —H, or —OH, or —OCH$_3$ and
where $R_2$ is —OH or —OCH$_3$

Examples of this class of compounds are:
  (a) 4,6-dihydroxy-2-aminopyrimidine
  (b) 4-methoxy-2-aminopyrimidine (4.) Those compounds which have the following general structure:

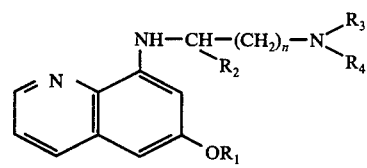

where $R_1$ = —H or —CH$_3$ and
where $R_2$ = —CH$_3$ or —C$_2$H$_5$ or —H and
where $R_3$ and $R_4$ = —H or —CH$_3$ and
where $n$ = 1, 2, or 3

An example of this general class of compounds is:
  (a) 8-(4-amino-1-methylbutylamino)-6-methoxyquinoline (5.) Those compounds which have the following general structure:

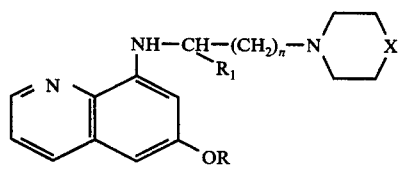

where
R = —H, or —CH$_3$ $R_1$ = —$CH_3$, or —$CH_2CH_3$ or —H or —$CH_2CH_2$—$CH_3$
X = O or C
n = 1, 2, or 3.
An example of this class is:
(a) 8-(2-N-morpholinoethylamino)-6-methoxyquinoline (6.) Those compounds which have the following general structure:

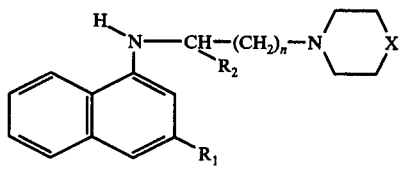

where $R_1$ = —H, —OCH, or —OH and
where $R_2$ = —H, —$CH_3$ or —$C_2H_5$ and
where X = O or C and
where n = 1, 2 or 3
An example of this class of compounds is:
(a) 2-N-morpholinoethyl-1-naphthylamine The chromogenic reagent is prepared by dissolving an appropriate amount of the chromogenic compound to be used in a solution containing approximately 4 mol/L of sulfuric acid, and a surfactant such as polyoxyethylene lauryl ether (such as BRIJ 35) or an alkylaryl polyether (such as TRITON) or any other non-ionic surface active agent in a final concentration of approximately 1-3%. The exact amount of chromogenic compound to be used will be established by the molarity of the o-phthalaldehyde reagent used in the particular application. The general guide lines are such that the molarity of the chromogenic compound should be ideally from about 0.1 to 1.0 times the concentration of the o-phthalaldehyde in the final reaction mixture. In general, the higher molar ratios of chromogenic compound to aldehyde may be used when the chromogenic compound does not possess a free amino group.

It will be understood that certain modifications and variations of the specific and general concepts of the invention may be effected without departing from the inventive concepts heretofore described.

Accordingly, the invention is not to be considered limited to the specific form or embodiments set forth herein for the purpose of disclosing and illustrating the inventive concepts discovered and herein applied.

For example, the preparation of the o-phthalaldehyde reagent is described as being prepared in a solution of 3.75 N sulfuric acid. This particular concentration of sulfuric acid has been found to provide an optimal balance between a desirable reaction rate and the use of a strong acid. One practiced in the art, however, may deviate from the use of the exact concentration of acid given without departing from the general concepts given herein. Similarly, one may substitute a particular non-ionic surfactant such as described in any standard text and yet not depart from the basic inventive concepts detailed.

In the embodiments given above, the chromogen compound has been made up in an 8 N sulfuric acid solution. However, one may deviate from the exact normality given in the above preferred embodiment without departing from the inventive concepts described. The general guide line for acid concentration departures is that either increasing or decreasing the acid concentration of this reagent will lead to a reduction in the rate of color development observed in the final reaction mixture. While considerable variation in acid concentration may be tolerated, sizeable decreases in acid concentration may lead to a significantly diminished rate of color development; the use of sizeable increases in acid strength may lead to diminished stability of reagent and the undesirable effects of exposing laboratory personnel and equipment to strong acids.

In the general guide lines for the preparation of the above reagents, it will be noted that both desirably include the use of a non-ionic surface active agent. The purpose of this surfactant may be twofold, depending upon the particular chromogenic substance used.

For example, the inclusion of a surface active agent will generally impart better flow characteristics to the reagent system, therefore providing a more acceptable reagent for those analysts that will make their absorbance readings in a photometer equipped with a flow cell (i.e., a system which uses a single cell to measure all absorbances with an automatic means of filling and emptying the contents of the cell).

The second function of the surfactant used is to facilitate the solubilization of the particular chromogenic compound used. While in theory all of the general classes of substances outlined will work, it has been discovered that the inclusion of a proper concentration of a surfactant may be necessary to aid in the solubilization of the particular compound used to obtain optimal results. For example when class 1 or class 2 compounds are used, it is necessary to include a proper concentration of surfactant to effect solubility and to prevent turbidity in the final reaction mixture.

EXAMPLES

EXAMPLE 1

PREPARATION OF REAGENT SYSTEM

An o-phthalaldehyde reagent was prepared by dissolving 2000 mg of o-phthalaldehyde in approximately 800 ml of 3.75 N sulfuric acid which contained 1 ml of a 25% solution of polyoxyethylene lauryl ether (BRIJ 35) and the reagent made to volume of 1 liter with 3.75 N sulfuric acid. The receptor reagent was prepared by dissolving 500 mg of 8-(4-amino-1-methylbutylamino)-6-methoxyquinoline phosphate in 800 ml of a solution containing 5.0 gm of boric acid, 222 ml of concentrated sulfuric acid, and 0.9 ml of a 25% solution of polyoxyethylene lauryl ether (BRIJ 35), and the resulting solution made to a final volume of one liter by addition of water.

ANALYTICAL PROCEDURE

The reagent system prepared as described above leads to a very rapid color development that is well suited to automated analysis.

In using this reagent system, approximately 30 microliters of a sample of body fluid are added to a reaction tube; and to it simultaneously are added approximately 1.8 ml of each of the above described reagents, and the resultant mixture is thoroughly mixed to insure homogeneity. The reaction mixture is then incubated at 37° C to further hasten the color development for a period of three minutes. The reaction mixture is then transferred to a spectrophotometer, and the absorbance of the resulting color is measured at a wavelength of 520 nm. The urea content of the patient's sample is then automatically calculated from the absorbance reading of a standard solution of urea which has been treated in an identical manner.

This particular reagent system and application has been shown to give linear results with serum samples containing as much as 150mg/dl of urea nitrogen, and to be virtually unaffected by sulfa drugs commonly used in the treatment of kidney dysfunctions.

EXAMPLE 2

PREPARATION OF REAGENTS

The o-phthalaldehyde reagent is prepared by dissolving approximately 2 grams of o-phthalaldehyde in one liter of 3.5 N sulfuric acid which contains 4 ml/L of TRITON X-100, and 1 ml/L of polyoxyethylene lauryl ether, (BRIJ 35) both of which are surfactants.

The receptor reagent is prepared by dissolving 1.8 gm of 1,3-dihydroxynaphthalene in one liter of 5N sulfuric acid containing 15 ml/L of TRITON X-100.

PROCEDURE

In this example, 20 microliters (0.02 ml) of a body fluid containing an unknown amount of urea is added to a tube containing 3.0 ml of the aldehyde reagent and mixed. One (1.0) ml of the receptor reagent, 1,3-dihydroxynaphthalene, is added and mixed. The resultant mixture is then incubated at 37° C for 10 minutes, and the absorbance developed is read in a spectrophotometer versus a reagent blank composed of 20 microliters of water, 3.0 ml of the aldehyde reagent and 1.0 ml of the 1,3-dihydroxynaphthalene reagent which has been treated in a similar manner, at a wavelength of 470 nm.

The absorbance of the unknown is then compared with the absorbance developed in a standard solution of urea nitrogen which has been treated identically to the unknown for purposes of calculating the urea content of the unknown.

EXAMPLE 3

All reagents are prepared as in Example 1 except that 600mg of N-morpholinoethyl-1-naphthylamine is substituted for the 500 mg of 8-(4-amino-1-methylbutylamino)-6-methoxyquinoline phosphate used in the chromogen reagent. This reagent system produces characteristics similar to those in Example 1 except that the final reaction product is read at a wavelength of 540 nm instead of 520 nm.

EXAMPLE 4

The reagents are prepared as in Example 2 with the exception that 1,880 mg of 1,3,5-trihydroxybenzene is substituted for the 1.8 gm of dihydroxynaphthalene used in the chromogen reagent. The performance characteristics and application of this system are essentially similar to those given in Example 2.

EXAMPLE 5

The reagents as prepared in Example 2 above with the exception that 291 mg of 4,6-dihydroxy-2-aminopyrimidine is substituted for the 1.8 gm of dihydroxynaphthalene used in the chromogen reagent. The performance characteristics and application of this system are essentially the same as those given in Example 2 above.

REFERENCES

1. Marshall, E. K., Jr.: *J. Biol. Chem.* 15:487 (1913)
2. Gentzkow, C. J.: *J. Biol. Chem.* 143:531 (1942)
3. Henry, R. J.: *Clinical Chemistry: Principles and Techniques,* New York, Harper & Row (1968) p. 513
4. Fearon, W. R.: *Biochem J.:* 33:902 (1939)
5. Ormsby, A. A.: *J. Biol. Chem.;* 146:595 (1942)
6. Brown, H. H., *Anal. Chem.* 31:1844 (1959)
7. Roijers, A. F. M. and Tas, M. M., *Clin. Chem. Acta,* 9:197 (1964)
8. Morin, L. G., and Prox, J., *Clin. Chem. Acta,* 47:27 (1973)
9. Jung et al. *Clin. Chem.,* 21:1136 (1975)
10. Merck Index, 8th Ed., p. 717 Merck and Co., Inc. (1968)

What is claimed is:

1. A process for the quantitation of urea in a fluid sample, in which the sample is reacted with a reagent containing an acidic solution of o-phthalaldehyde and an acidic solution of a chromogenic compound of the general class consisting of 1, or 1,3-mono- or di-substituted hydroxy or methoxy naphthalene compounds which have the following general formula:

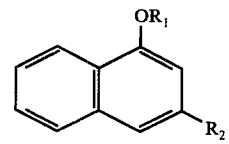

where $R_1 =$ —H, or —CH$_3$ and
where $R_2 =$ —H, or —OH, or —OCH$_3$.

2. The process as defined in claim 1, in which the chromogenic compound used is 1,3-dihydroxynaphthalene.

3. The process as defined in claim 1, in which the chromogenic compound used is 1-hydroxynaphthalene.

* * * * *

UNITED STATES PATENT OFFICE
CERTIFICATE OF CORRECTION

Patent No. 4,105,408　　　　　　　　　Dated August 8, 1978

Inventor(s) Jerry W. Denney

It is certified that error appears in the above-identified patent and that said Letters Patent are hereby corrected as shown below:

Column 2, Line 51: The word "to" should read "the"

Column 5, Line 22: The words "of a" should read "to 2000 mg of"

Column 10, Line 34: The expression "1,3-mono-" should read "1,3 mono-"

Signed and Sealed this

Twenty-seventh Day of March 1979

[SEAL]

Attest:

RUTH C. MASON
*Attesting Officer*

DONALD W. BANNER
*Commissioner of Patents and Trademarks*